United States Patent
Litten-Brown et al.

(10) Patent No.: US 9,393,334 B2
(45) Date of Patent: Jul. 19, 2016

(54) LIQUID TRANSFER AND EVAPORATION DEVICE

(75) Inventors: Colin Litten-Brown, Bracknell (GB); Guy Edward Naish, Bicester (GB); Anjum Fatima Shaukat, Twickenham (GB); Richard P. Sgaramella, Hoboken, NJ (US)

(73) Assignee: Givaudan S.A., Vernier (CH)

( * ) Notice: Subject to any disclaimer, the term of this patent is extended or adjusted under 35 U.S.C. 154(b) by 1102 days.

(21) Appl. No.: 12/278,250

(22) PCT Filed: Feb. 27, 2007

(86) PCT No.: PCT/CH2007/000099
§ 371 (c)(1),
(2), (4) Date: Sep. 16, 2008

(87) PCT Pub. No.: WO2007/098627
PCT Pub. Date: Sep. 7, 2007

(65) Prior Publication Data
US 2010/0237162 A1 Sep. 23, 2010

Related U.S. Application Data

(60) Provisional application No. 60/777,925, filed on Mar. 1, 2006, provisional application No. 60/793,742, filed on Apr. 21, 2006.

(51) Int. Cl.
| | |
|---|---|
| *A61L 9/12* | (2006.01) |
| *A61L 9/04* | (2006.01) |
| *A61M 1/20* | (2006.01) |
| *A01M 1/20* | (2006.01) |
| *A61L 9/03* | (2006.01) |

(52) U.S. Cl.
CPC .............. *A61L 9/127* (2013.01); *A01M 1/2044* (2013.01); *A61L 9/037* (2013.01); *Y10T 29/49826* (2015.01)

(58) Field of Classification Search
USPC .......... 239/6, 34, 44–50, 326; 428/15, 17, 18, 428/22, 23, 35.6, 905
See application file for complete search history.

(56) References Cited

U.S. PATENT DOCUMENTS 3,587,968 A * 6/1971 Hennart et al. ................. 239/47
5,077,102 A 12/1991 Chong
(Continued)

FOREIGN PATENT DOCUMENTS

| WO | WO03092750 A | 11/2003 | |
| WO | WO 03092750 A1 * | 11/2003 | ................ A61L 9/12 |
| WO | WO2004/082726 A | 9/2004 | |

(Continued)

OTHER PUBLICATIONS

Pierce Arnold Natural Qualit: Shola log withour Skin Online; May 1, 2005; Retrieved from the internet: www.piercearnold.co.uk/product.php?pic=614.

*Primary Examiner* — Darren W Gorman
(74) *Attorney, Agent, or Firm* — Curatolo Sidoti Co., LPA; Salavatore A. Sidoti; Floyd Trillis, III

(57) ABSTRACT

Devices having one or more transfer elements (wick, emanator) formed from plant material derived from the stems of sola plants from the genus *Aeschynomene L.*, family Fabaceae in air fresheners or evaporation devices for other actives (fragrances, insecticides, fungicides, pharmaceuticals). Methods of assembling a device having one or more transfer elements (wick, emanator) formed from plant material derived from the stems of sola plants from the genus *Aeschynomene L.*, and for using the device to transfer or evaporate liquids containing active are also provided. The material when used in form of a wick or emanator shows excellent liquid transfer and of both aqueous and non-aqueous liquids and a low fractionation of a mixture of actives.

17 Claims, 1 Drawing Sheet

(56) References Cited

U.S. PATENT DOCUMENTS

2005/0284952 A1 12/2005 Davis et al.
2006/0289669 A1 12/2006 McGee et al.

FOREIGN PATENT DOCUMENTS

| WO | WO2005021055 A | 3/2005 |
| WO | WO2006002404 A | 1/2006 |

* cited by examiner

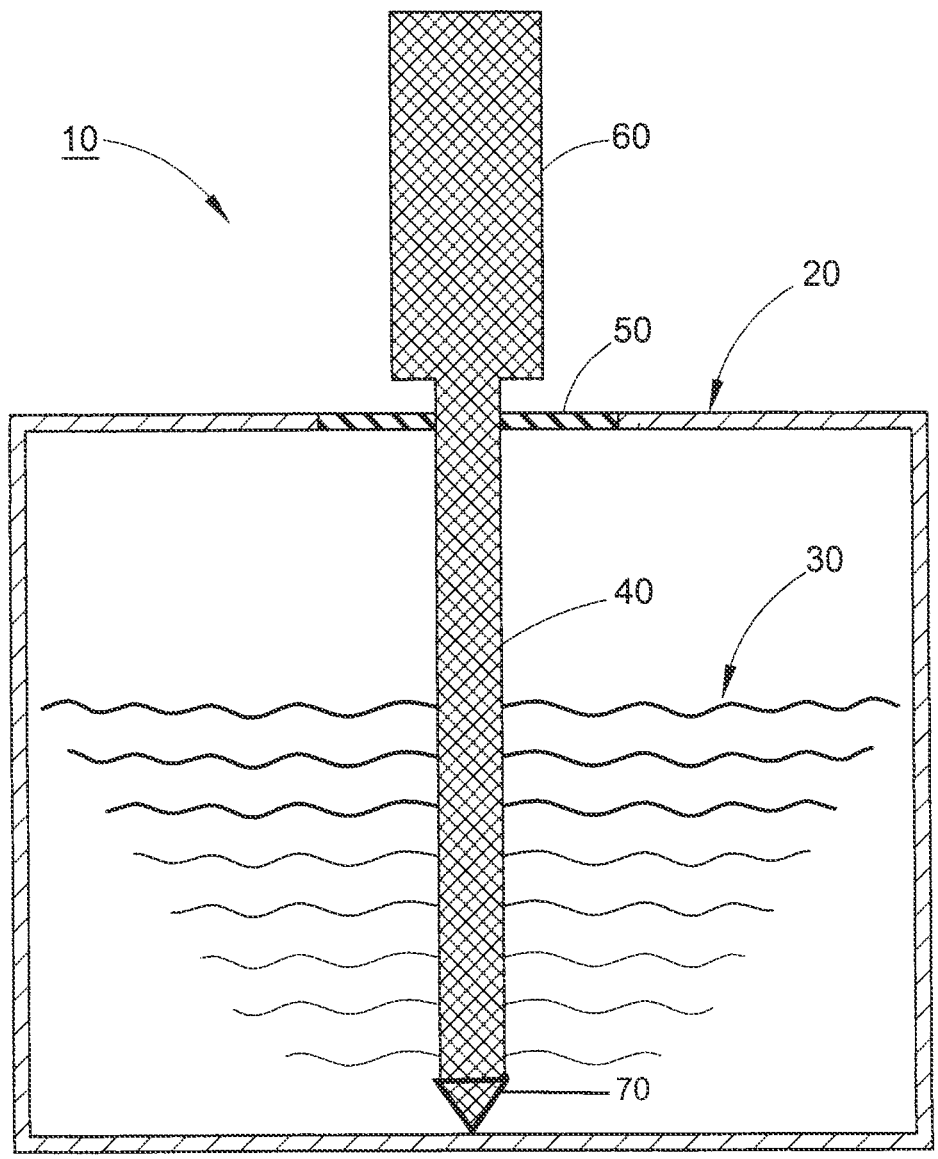

LIQUID TRANSFER AND EVAPORATION DEVICE

TECHNICAL FIELD

Transfer elements made of plant stem material and their use for the transfer and evaporation of liquids comprising actives, such as fragrances, insecticides, fungicides, and pharmaceuticals are provided.

BACKGROUND

Examples of commonly used wick materials are cellulose, either in the form of cardboard (pressed pulp) or fibres; porous plastic, in particular those made by POREX™ (Porex Technologies, Fairburn, US) or Micropore Plastics (Royal Woods Parkway Tucker, Ga., US), and others; graphite; and ceramic.

There is a trend in the industry to use natural materials, as consumers will often prefer these. Some plant stem materials, in particular bamboo and rattan, are known to function as wicks.

The transfer or evaporation rate of a liquid through a particular wick material depends to a considerable extent on the nature of the liquid, the difference between aqueous and non-aqueous liquids being particularly marked. The degree of absorbency of all of these wick materials in a given liquid is also variable. Thus, different wick materials are selected for different applications, depending on the nature of the liquid desired to be transferred.

Many common wick materials, such as porous plastic and rattan, have a limited porosity and transfer or evaporation rate, partially due to blocking or slow transfer of at least part of fragrance ingredients (for example due to fractionation and/or blocking).

Fractionation over time will change the character and/or intensity of the fragrance and will slow evaporation. Particularly problematic in terms of evaporation properties including the occurrence of fractionation are fluids comprising actives that, for example, occur in crystalline form in nature, have a high molecular weight, or low vapour pressure.

Similarly, there is a need for emanators that provide for efficient transfer and evaporation of a liquid received by contact to a wick.

Therefore, there remains a need for a transfer element (wick, emanator) material that has a good absorbency and can efficiently transfer both aqueous and non-aqueous liquids comprising the abovementioned actives at a good evaporation rate without significant fractionation.

SUMMARY

A method of disseminating a volatile liquid from a reservoir into an atmosphere comprising transferring and evaporating the liquid by means of one or more transfer elements comprising a wick and/or an emanator, wherein at least one of the one or more transfer elements comprises dried plant stem material from a sola plant of the genus *Aeschynomene L.*

A wick for a device for the transfer and evaporation of volatile liquid, said wick comprising dried plant stem material from a sola plant of the genus *Aeschynomene L.*

An emanator for a device for the transfer and evaporation of volatile liquid, said emanator comprising dried plant stem material from a sola plant of the genus *Aeschynomene L.*

A device for the transfer and evaporation of a volatile liquid comprising:

a reservoir for said volatile liquid; and
one or more transfer elements comprising a wick and/or an emanator, wherein at least one of the one or more transfer elements comprises dried plant stem material from a sola plant of the genus *Aeschynomene L.*

A method of providing a device as described-hereinabove comprising assembling at least one of the one or more transfer elements and the reservoir into the device.

A device for the transfer and evaporation of a volatile liquid provided in the form of a combination of its components a) and b) ready for assembly upon use, comprising:

a) a sealed reservoir filled with a volatile liquid; and
b) one or more transfer elements comprising a wick and/or an emanator, wherein at least one of the one or more transfer elements of component b) comprises dried plant stem material from a sola plant of the genus *Aeschynomene L.* for transfer of said volatile liquid.

A method of providing the device as herein-above described comprising assembling the reservoir and at least one of the one or more transfer elements to provide said device upon first use.

BRIEF DESCRIPTION OF DRAWINGS

FIG. 1 depicts an illustrative embodiment of the device for transfer and evaporation of a volatile liquid.

DETAILED DESCRIPTION

Applicant has now identified a plant stem material that, surprisingly, has the desired properties of being able to efficiently transfer both aqueous and non-aqueous liquids comprising actives at a good evaporation rate without significant fractionation and which shows an excellent performance when used as a transfer element (wick or emanator).

A transfer element transfers a volatile liquid to be disseminated into an ambient atmosphere. Transfer elements include wicks and emanators.

A wick is a transfer element that transfers a volatile liquid from a volatile liquid reservoir to a surface where the volatile liquid evaporates into an ambient atmosphere, or to an emanator.

An emanator is a transfer element that transfers volatile liquids from a wick into an ambient atmosphere by evaporation.

According to certain illustrative embodiments, air fresheners and insecticide devices, liquid is transferred from a reservoir to the air by evaporation from the surface of the wick or an associated emanator with a separate diffusing surface. The wick and/or emanator comprise plant stem material. The porous element used to achieve the transfer from the reservoir to the emanator/air is commonly referred to as a wick.

To disseminate a volatile liquid from a reservoir into an atmosphere, a wick can be used as sole transfer element, with the liquid evaporating from the wick surface.

Alternatively, the wick may be in contact with an emanator, whereby the wick transfers the liquid from the reservoir through the wick to the emanator and evaporation is enhanced by the larger surface of the emanator.

Still alternatively, the wick may be formed in a shape to provide an enlarged surface-area itself from which the liquid can evaporate, so that no emanator is needed.

The plant stem material that is useful for preparing the wick and/or emanator is taken from plants of the genus *Aeschynomene L.* from the family *Fabaceae*. The genus includes a number of species often called jointvetch, shola or sola, for example *Aeschynomene afraspera* (sola pith),

*Aeschynomene americana* (American joint-vetch, joint-vetch or pega pega), *Aeschynomene aspera* (sola pith plant, sola), *Aeschynomene falcate* (Australian joint-vetch), *Aeschynomene indica* (curly indigo, hard sola, Indian joint-vetch, kat sola, northern joint-vetch, or sensitive joint-vetch) and *Aeschynomene villosa*. The stem material of sola plants is very light in weight and contains a characteristic central pith.

Throughout this application, the abovementioned plants are referenced as "sola" or "sola plants." Sola plants are found growing around the world, usually in wet regions such as rice fields and are often regarded as weeds. The stems of the sola plant, usually stripped of the outer skin, are used in a number of decorative household items and are commonly processed into decorative shapes. The stems are commercially available cropped (usually by hand) to rods of average diameter from 20-50 mm with variable and irregular cross-sections.

In a first aspect, there is provided a method of disseminating a volatile liquid from a reservoir into an atmosphere. The method comprises transferring and evaporating the liquid by means of one or more transfer elements. The transfer elements may be selected from a wick and an emanator, wherein at least one of the one or more transfer elements comprises dried plant stem material from a sola plant of the genus *Aeschynomene L*. In certain embodiments, the transfer elements are selected from the group consisting of a wick, emanator, and combinations thereof.

According to further embodiments, there is provided a method as hereinabove described wherein at least one of said one or more transfer element comprises dried plant stem material from a sola plant selected from the group consisting of *Aeschynomene afraspera, Aeschynomene americana, Aeschynomene aspera, Aeschynomene falcate, Aeschynomene indica, Aeschynomene villosa*, and combinations thereof.

According to still further embodiments, a method as hereinabove described is provided, wherein the volatile liquid comprises one or more actives selected from the group consisting of fragrance, insecticide, fungicide, pharmaceutical, and combinations thereof.

In another aspect, there is provided a wick for a device for the transfer and evaporation of volatile liquid into an atmosphere. The wick for the device comprises dried plant stem material from a sola plant of the genus *Aeschynomene L*.

According to further embodiments, the wick for the device comprises dried plant stem material from a sola plant selected from the group consisting of *Aeschynomene afraspera, Aeschynomene americana, Aeschynomene aspera, Aeschynomene falcate, Aeschynomene indica, Aeschynomene villosa*, and combinations thereof.

In another aspect, there is provided an emanator for a device for the transfer and evaporation of volatile liquid. The emanator comprises dried plant stem material from a sola plant of the genus *Aeschynomene L*.

According to further embodiments, the emanator comprises dried plant stem material from a sola plant selected from the group consisting of *Aeschynomene afraspera, Aeschynomene americana, Aeschynomene aspera, Aeschynomene falcate, Aeschynomene indica, Aeschynomene villosa*, and combinations thereof.

In another aspect, there is provided a device for the transfer and evaporation of a volatile liquid. The device for the transfer and evaporation of a volatile liquid comprises a reservoir for containing the volatile liquid and one or more transfer elements comprising a wick and/or an emanator. Either or both of the wick and emanator transfer elements comprise dried plant stem material from a sola plant of the genus *Aeschynomene L*.

According to certain embodiments, the device for the transfer and evaporation of a volatile liquid into an atmosphere is a device wherein at least one of the transfer elements comprises dried plant stem material from a sola plant selected from the group consisting of *Aeschynomene afraspera, Aeschynomene americana, Aeschynomene aspera, Aeschynomene falcate, Aeschynomene indica, Aeschynomene villosa*, and combinations thereof.

According to other embodiments, the device as hereinabove described is a device wherein the reservoir of the device is filled with a liquid comprising one or more actives. The actives filled in the reservoir of the device may be selected from a fragrance, an insecticide, a fungicide, a pharmaceutical, and combinations thereof.

In another aspect, there is provided a method of providing a device as hereinabove described comprising assembling at least one of the one or more transfer elements and the reservoir to provide the device.

In still another aspect, there is provided a device for the transfer and evaporation of a volatile liquid provided in form a combination of its components a) and b) ready for assembly upon use. The combination of components a) and b) comprise a) a sealed reservoir filled with a volatile liquid; and b) one or more transfer elements selected from a wick and an emanator. At least one of the one or more transfer elements of component b) comprises dried plant stem material from a sola plant of the genus *Aeschynomene L*. for transfer of said volatile liquid.

According to further embodiments of the device for the transfer and evaporation of a volatile liquid, the one or more transfer elements are provided at least at one end with a point-like structure that is sufficiently pointed to be punched through the seal of the reservoir by manual pressure.

According to still further embodiments of the device for the transfer and evaporation of a volatile liquid, the point-like structure of the one or more transfer elements is provided by modification of the form of the wick to provide the point-like structure, or by addition of a second material to the transfer element provide the point-like structure.

According to yet further embodiments of the device for the transfer and evaporation of a volatile liquid, the reservoir is filled with a liquid comprising one or more actives selected from fragrance, insecticide, fungicide, pharmaceutical, and combinations thereof.

In another aspect, there is provided a method of providing a device for the transfer and evaporation of a volatile liquid comprising assembling the reservoir and at least one of the one or more transfer elements to provide the device upon first use.

In still another aspect, there is provided the use of dried plant stem material from a sola plant of the genus *Aeschynomene L*. as a transfer element in a device for the transfer of a volatile liquid.

According to further embodiments, there is provided a use as hereinabove described wherein the transfer element is selected from the group consisting of a wick, an emanator, and combinations thereof.

Without limitation, in certain illustrative embodiments, there are provided devices and methods as described hereinabove wherein the volatile liquid comprises one or more actives selected from fragrance, insecticide, fungicide, pharmaceutical, and combinations thereof.

The sola stems may be used as wicks in dried, crude form, or they may be first sanded or shaved. Alternatively, they may be shaped by any convenient means to give rods of regular cross-section. Such means include, for example, routing, sawing, planing, cutting, lathing or forming in a die. The regular cross-section may by any desired shape, such as circular, elliptical, square, rectangular or polygonal.

Thus, the plant stem material from the sola plants can be readily formed into appropriate sizes and shapes suitable for wicks. For example, sola wicks with diameters of 2-20 mm (+/−0.25-1.0 mm) and a length of 2 to 60 cm, for example 2 to 15, or 3 to 10 cm, may be used as a transfer element in a device for the transfer and evaporation of a volatile liquid into an atmosphere.

By these methods, rods of regular and even cross-section are achieved. Such rods may be formed from crude plant stems or commercially purchased with an evened out cross-section and in the desired length and diameter.

A sola stem may be selected according to length and diameter so that it can be inserted into a reservoir, which contains a liquid to be transferred. The stem may enter the reservoir through a suitable orifice, either directly or via a liquid-tight insert fitting into the orifice. Such an insert may be of any suitable material that is not affected by the liquid, for example solvent-resistant plastics, which include, for example, polypropylene, polyethylene and the like. The insert may have a hole slightly smaller than the wick diameter and the wick is inserted with a tight fit as slight compression of the wick does not impair performance. Alternatively, the insert can be formed of a 2-piece or hinged unit that clips around the wick before insertion into the bottle.

The wick may itself act as the emanator for the liquid, or it may be associated with an emanating surface for which it acts as the transfer medium for the liquid from the reservoir to this emanating surface. The emanating surface may be any suitable surface made of any suitable material. For example, it may be an absorbent surface in liquid transfer contact with and extending from the surface of the stem. Such absorbent surfaces may be self-supporting, for example, cardboard, or supported, for example, a fibrous material supported on a plastic surface. It may also be a capillary sheet of the type described in WO 2004/082726.

Optionally, to a wick as hereinabove described, the device may comprise an emanator formed from sola plant stem material as hereinabove described. The emanator may be formed in any shape. As will be apparent to the skilled person, the shape should have a high surface area to facilitate evaporation. For example, various flower-like shapes including petal-shaped chips of sola stems arranged to form a rose-shaped structure are suitable and provide a functional as well as aesthetically pleasing emanator.

The emanator may be used with a wick as described hereinabove, or a conventional wick, for example a wick made of porous material well known in the art may be used.

One example is a rod-shaped wick without an additional emanator structure that evaporates the liquid from the wick surface. Alternatively the liquid may be evaporated by an emanator, for example in the shape of a flower. Another example is a wick that is itself rose-shaped and may be floating on a "pond-type" reservoir that is wider than its height, wherein the bottom part is exposed to the liquid, and transfers the liquid through the structure to the petal-shaped evaporation surface at the top part of the structure.

The emanator provides an emanating surface that comprises material of sola plant stems as described hereinabove. This emanating surface may be constructed of a number of single elements and formed in such a way as to resemble a flower head or other decorative structure. The elements may be of identical, similar or different shape. The elements can be affixed to each other with a suitable affixing means including, for example, mechanical and chemical affixing means, in any suitable way to form an emanator. For example, they may be bound or tied together (for example by suitable bindings including thread, string, wire or tape); glued together by adhesive, stapled together, or affixed using pins or other affixing means. When glue or adhesive is used, care should be taken not to impair the transfer of liquid between wick and emanator. Alternatively, a number of single elements may be inserted into a common element formed from sola material that holds the other single elements together. Still alternatively, the single elements may be inserted/plugged into each other or into a wick, optionally using additional affixing means. For example, the upper end of the wick and the lower portion of the emanator could be fitted with rigid docking pieces that fit together and, in doing so, bring the wick and emanator into intimate contact.

The lowest portion of said emanator is arranged such in the device that it is exposed to the liquid or can contact a (usually upper) portion of the wick to allow liquid transfer. Ideally, any elements of the emanator not in direct contact with the wick should be in direct contact with elements that are in contact with the wick to allow liquid transfer between elements. The affixing means should be arranged in such a way as to avoid hindering of the liquid transfer. The emanator can be placed on top of a wick extending from a reservoir of liquid. The emanator can be kept in place relying of gravity or secured to the wick and/or to the reservoir by any suitable means, for example as described hereinabove for affixing the single elements comprised in the emanator. The skilled person will be aware that when using affixing means that potentially can hinder the liquid transfer, care must be taken to place the affixing means accordingly, for example a connector may be glued to a portion, for example an outside portion, of wick and emanator so as to leave another portion, for example an inside portion, free for liquid transfer.

The emanator may be contained within an open, closed or partly closed protective support, cover or cage. The protective support, cover or cage may, for example, be formed of a mesh, grill or transparent material so that the emanator can be seen but not touched and contact of consumer to the liquid is avoided. The protective support, cover or cage can be attached by any suitable means. A sufficiently heavy cage will be held in place by gravity when placed on the reservoir. Alternatively, various affixing means may be used as will be apparent to the skilled person, for example a screw thread mechanism or clip mechanism to the liquid reservoir, or any of the affixing means described hereinabove.

Transfer elements (wicks and emanators) of sola plant stems as hereinabove described can easily be used various types of well-known devices for the transfer and evaporation of volatile liquids. These devices typically comprise a reservoir adapted to store volatile liquid and a porous element for transfer of the volatile liquid (wick), and optionally an emanator. The wick may directly provide the volatiles to the atmosphere via an evaporation surface. Alternatively, evaporation may be assisted by additional means, for example by an additional evaporation surface in contact to the wick so that the volatile liquid is transferred to be evaporated from the additional surface (for example a sheet or screen of porous and/or capillary material as described in WO 2005/044321 and WO 01/23008, or an emanator formed from sola plant material as hereinabove described). Additionally or alternatively, an air current can be generated by a fan or heat can be applied to speed up evaporation.

The reservoir and wick may be rendered spillage-proof by employing a seal and/or by providing that the wick fits tightly into the reservoir at the place where it leaves the reservoir. For example, a sleeve surrounding at least part of the wick as described in WO03092750 and WO0123008 may be present.

The sleeve fits in with the opening of the reservoir and optionally an additional sealing means to provide a tight fit and seal the reservoir opening against spillage, and prevent or lessen spillage through the wick when the device is tilted or turned. The sleeve is made of a material impervious to the volatile liquid, and it surrounds at least a part of the wick but leaves the top and bottom portion free for liquid transfer and/or evaporation.

In the case of a complete sealing of the wick within the opening of the reservoir, a pressure vent in the reservoir may be needed to equilibrate pressure when the device is in operation.

The transfer element (wick and/or emanator) may be pre-inserted into the liquid reservoir, for example within a filled reservoir that may be sealed or provided with a cap against spillage, or within a reservoir without liquid, which is adapted to receive ato a cartridge or refill comprising the liquid.

Alternatively, the transfer element (wick and/or emanator) is provided in combination with a closed (sealed or capped) reservoir with volatile liquid, with instructions that the wick and/or emanator be inserted into the reservoir by the consumer upon first use. For example, the liquid reservoir may be provided with a breakable seal through which the wick and/or emanator is inserted. To break the seal more easily, the wick may be provided with one end adjusted to form a point. This may be reached by taking away wick material to form a point by any convenient method (for example sawing, cutting, splicing, shaving, sanding), or by providing the wick and/or emanator with a pointed end made of sola plant stem material or another material, for example plastic or metal. A cap may be provided to cover the wick and/or emanator and stop evaporation when not in use.

FIG. 1 shows an illustrative embodiment of the device employed in the method. The device (10) includes a reservoir (20) suited for containing a quantity of volatile liquid (30). The device (10) includes a wick (40) in fluid contact with the liquid (30) contained within the reservoir (20). The reservoir (20) includes a disruptable seal (50) to provide a vapor tight barrier between the upper portion of the wick (40) and the ambient environment. The emanator (60) is adapted to be in fluid communication with the atmosphere and allows for the transfer and evaporation of volatile liquid (20) from reservoir (20). Another illustrative embodiment of a flower-shaped emanator (90) is shown. The flower-shaped emanator (90) facilitates transfer and evaporation of volatile liquid (20) into the atmosphere. The porous wick (40) may terminate in a point-like structure (70).

There now follows a series of non-limiting examples that serve to further illustrate the devices and methods. The illustrative examples should not be construed to limit the devices and methods in any manner.

EXAMPLES

Example 1

Liquid Absorbency of Different Wick Materials

Different wick materials were compared for absorbency of water, ethanol, and fragrance oil.

The wick materials tested were sola (plant stem material), rattan (plant stem material), fibrous cellulose (material derived from plants), cellulose card, and porous plastic. The sola & rattan are commercially available from Pierce Arnold, Wallington, UK. The cellulose fibre wick is commercially available from Filtrona, Milton Keynes, UK. The cellulose card was 500 gsm beermat board from Warren Package, Henley-on-Thames, UK. The porous plastic is 70-120 micron HDPE (POREX™, Porex Technologie GmbH, Singwitz, Germany).

As the fragrance oil, the following non-aqueous fragrance oil mixture based on glycol ether solvents was used:

| Compound | Wt % |
|---|---|
| Aldehyde C10 | 0.2 |
| Aldehyde C7 | 0.14 |
| Allyl caproate | 0.3 |
| Benzyl Acetate | 12.5 |
| Benzyl Propionate | 0.4 |
| Citonellyl Propionate | 1.5 |
| Dihydro Linalool | 4.0 |
| Hedione | 4.0 |
| Beta Ionone | 2.0 |
| Linalyl Acetate | 4.0 |
| *Litsea Cubeba* | 5.0 |
| Orange Oil | 8.0 |
| Vertenex | 2.0 |
| Pelargol | 4.0 |
| Tetrahydro Linalool | 15.0 |
| Solvent (Glycol Ether) | 37.0 |
| Total | 100.0 |

An amount of the dry absorbent material was weighed, immersed in the test liquid for 1 minute, removed from the liquid, allowed to drip for 1 minute and then re-weighed. From the determined masses, absorbency was calculated by dividing the mass of the wick material with liquid by the mass of the dry wick material and expressed as grams of liquid per gram of dry wick material.

The results are shown in Table 1 below.

TABLE 1

| Wick Material | Water Absorbency | Ethanol Absorbency | Fragrance Oil Absorbency |
|---|---|---|---|
| Sola | 3.50 | 14.50 | 15.50 |
| Rattan | 0.67 | 0.29 | 0.27 |
| Cellulose card | 2.76 | 0.81 | 1.40 |
| Cellulose fibre | 1.85 | 1.83 | 2.08 |
| Porous plastic | 0.06 | 0.50 | 0.56 |

As can be seen in Table 1 above, the absorbency of sola towards all three test liquids is significantly higher than all other wick materials tested.

Rattan has the poorest overall absorbency of all the liquids, but is slightly preferential towards water. Porous plastic also exhibited a low absorbency, but was preferential towards non-aqueous liquids. The cellulose materials exhibited a slightly higher absorbency than rattan or porous plastic. The card cellulose material is formed of pulp and tends towards water absorbency, whereas the cellulose in form of fibres tends towards oil/non-aqueous liquids absorbency.

Example 2

Evaporation/Liquid Transfer of Fragrance Oil of Different Wick Materials

The evaporation rate of fragrance oil from different wick materials was determined as evidenced by mass loss after 12 days, as follows.

For each wick material, cylindrical sections with a circumference equivalent to approximately 25 mm were inserted into a reservoir containing fragrance oil and sealed around the neck of the reservoir bottle using laboratory film. A length (40 mm) of each material was left exposed above the sealant film. Duplicates were prepared for each wick material test, and one of these was weighed and then left in ambient room conditions, the other was weighed and then left in the direct constant air flow of a small impeller mounted on a 1.5V DC motor. The porous plastic material was POREX™ HDPE moulded plastic with an average porosity of 30 microns.

After 12 days, the total weight loss was determined in grams. Table 2 shows the results.

TABLE 2

Evaporation of fragrance oil from various wick materials as evidenced by weight loss after 12 days

|  | Weight loss ambient conditions | Weight loss with Fan |
|---|---|---|
| Sola | 4.28 | 5.12 |
| Rattan (plant stem) | 0.91 | 0.99 |
| Cellulose Fibre | 3.66 | 4.20 |
| Porous Plastic | 1.83 | 1.69 |

The sola material exhibited the best performance of all materials tested both under ambient and fan-assisted conditions. Rattan and porous plastic were able to evaporate considerably less fragrance oil, after the sola material. Cellulose in form of fibres performed better than rattan or porous plastic.

Example 3

Fractionation of Fragrance Oil in Different Wick Materials

The fragrance fractionation properties of wick materials as in example 2 and a wick with external capillaries as described in U.S. Pat. No. 4,913,350 were compared.

The multi-component test composition of the fragrance is given below. The test composition contained selected ingredients known in the art to be difficult to evaporate through wicks without fractionation or similar effects occurring (for example due to their crystal form, high molecular weight or vapour pressure).

| Fragrance Composition | Wt % |
|---|---|
| Fragrance ingredients: | 39% |
| Benzyl Acetate | 3 |
| Benzyl Salicylate | 3 |
| Coumarin | 3 |
| Cuminic Aldehyde | 3 |
| Ethyl vanillin | 3 |
| Eugenol acetate | 3 |
| Hedione | 3 |
| Hexyl cinnamic aldehyde | 3 |
| Linalool | 3 |
| Methyl anthranilate | 3 |
| Methyl cedryl ketone | 3 |
| Distilled orange terpene | 3 |
| Peach Pure | 3 |
| Solvent: Dowanol DPM Glycol Methyl Ether | 61% |

5 grams of fragrance was placed in a reservoir. A wick was placed into the reservoir in contact with the liquid and the system was sealed by applying aluminium foil around the exposed wick to seal the reservoir and leave the top end of the wick exposed to the ambient air. The test was incubated for 20 days at room temperature.

At then end of this period 0.5 inches or 1.25 cm of the top end of the exposed wick were cut off and the fragrance ingredients were extracted with methylene chloride.

A sample of the fragrance remaining in the reservoir and the methylene chloride extract from the wick were analyzed by GC/MS. Thereby, each fragrance ingredient was identified and quantified in relation to the other fragrance ingredients and the percent change of the fragrance ingredient (with exception of the volatile solvent) was calculated to determine the percent of the fragrance composition which had fractionated as follows:

$100 (F_o-F_w)/F_o = \%$ fractionation, with $F_o$ representing the fragrance ingredient in g in the liquid of the reservoir, and $F_w$ representing the fragrance ingredient in g in the wick. The % fractionation was calculated for each fragrance ingredient separately, then the mean of the fractionation of all fragrance ingredients was determined.

When no fractionation occurs, $F_w$ equals $F_o$ and the fractionation will be 0% according the above formula. A fractionation of 0% accordingly means that the ratios of fragrance ingredients in wick and reservoir are identical, and the ratio of fragrance ingredients in the wick has not changed compared to the one in the reservoir. The higher the fractionation percentage, the more change in ratios of the fragrance composition has occurred.

The following results were obtained:

|  | % fractionation of the fragrance composition |
|---|---|
| Sola | 4 |
| External capillary | 7 |
| Rattan | 51 |
| POREX ™ | 23 |
| Cellulose Fiber | 60 |

A very low fractionation shows the excellent performance of the sola wick compared to all other tested wick materials, both natural and artificial, and even wick constructions especially designed to avoid fractionation (external capillary).

While the transfer elements (wick and emanator), devices incorporating the transfer elements, and methods have been described above in connection with certain illustrative embodiments, it is to be understood that other similar embodiments may be used or modifications and additions may be made to the described embodiments for performing the same function. Further, all embodiments disclosed are not necessarily in the alternative, as various embodiments may be combined to provide the desired characteristics. Variations can be made by one having ordinary skill in the art without departing from the spirit and scope of the disclosure. Therefore, the transfer elements, devices and methods should not be limited to any single embodiment, but rather construed in breadth and scope in accordance with the recitation of the attached claims.

The invention claimed is:

1. A method of disseminating a volatile liquid from a reservoir into an atmosphere comprising:
   (i) contacting said volatile liquid in said reservoir with one or more transfer elements, or exposing one or more transfer elements that are in contact with said volatile liquid in said reservoir to the atmosphere;
   (ii) transferring said volatile liquid from said reservoir by means of said one or more transfer elements; and
   (iii) evaporating said volatile liquid from said one or more transfer elements, wherein at least one of the one or more of said transfer elements comprises dried plant stem material from a sola plant of the genus *Aeschynomene L.*

2. The method of claim 1, wherein said one or more transfer elements are selected from the group consisting of a wick, an emanator, and combinations thereof.

3. The method of claim 2, wherein at least one of said one or more transfer elements comprises dried plant stem material from a sola plant selected from the group consisting of *Aeschynomene afraspera, Aeschynomene americana, Aeschynomene aspera, Aeschynomene falcate, Aeschynomene indica, Aeschynomene villosa*, and combinations thereof.

4. The method of claim 1, wherein said volatile liquid comprises one or more actives selected from the group consisting of fragrance, insecticide, fungicide, pharmaceutical, and combinations thereof.

5. A device for the transfer and evaporation of a volatile liquid comprising:
   a reservoir for said volatile liquid; and one or more transfer elements, wherein at least one of the one or more transfer elements comprises dried plant stem material from a sola plant of the genus *Aeschynomene L.*

6. The device of claim 5, wherein said one or more transfer elements are selected from the group consisting of a wick, an emanator, and combinations thereof.

7. The device of claim 6, wherein at least one of the one or more transfer elements comprises dried plant stem material from a sola plant selected from the group consisting of *Aeschynomene afraspera, Aeschynomene americana, Aeschynomene aspera, Aeschynomene falcate, Aeschynomene indica, Aeschynomene villosa*, and combinations thereof.

8. The device of claim 5, wherein said reservoir is filled with a liquid comprising one or more actives selected from the group consisting of fragrance, insecticide, fungicide, pharmaceutical, and combinations thereof.

9. A device for the transfer and evaporation of a volatile liquid provided in the form of a combination of its components a) and b) ready for assembly upon use, comprising:
   a) a sealed reservoir filled with a volatile liquid; and
   b) one or more transfer elements, wherein at least one of the one or more transfer elements of b) comprises dried plant stem material from a sola plant of the genus *Aeschynomene L.* for transfer of said volatile liquid.

10. The device of claim 9, wherein said one or more transfer elements are selected from the group consisting of a wick, an emanator, and combinations thereof.

11. The device of claim 10, wherein said one or more transfer elements is provided at least at one end with a point-like structure sufficiently pointed to be punched through the seal of the reservoir by manual pressure.

12. The device of claim 10, wherein a point-like structure is provided by modification of the form of the wick to provide said point-like structure, or by addition of a second material to provide said point-like structure.

13. The device of claim 10, wherein said reservoir is filled with a liquid comprising one or more actives selected from the group consisting of fragrance, insecticide, fungicide, pharmaceutical, and combinations thereof.

14. A method of providing a device as defined in claim 5, comprising assembling at least one of the one or more transfer elements and the reservoir to provide the device.

15. A method of providing a device as defined in claim 9, comprising assembling of the reservoir and at least one of the one or more transfer elements to provide said device upon first use.

16. A method for the transfer of a volatile liquid comprising providing a transfer element comprising dried and sanded, shaved, shaped, or stripped plant stem material from a sola plant of the genus *Aeschynomene L*; contacting said volatile liquid in a reservoir with said transfer element; transferring said volatile liquid to said transfer element; and evaporating said volatile liquid from said transfer element.

17. The method of claim 16 wherein the transfer element is selected from the group consisting of a wick and an emanator.

\* \* \* \* \*